United States Patent [19]

Eden et al.

[11] Patent Number: 5,759,847

[45] Date of Patent: Jun. 2, 1998

[54] SYSTEM AND APPARATUS FOR AUTOMATICALLY TRANSFERRING MEDIA

[75] Inventors: Ruth F. Eden, Ann Arbor, Mich.; Steven H. Boyd, Falmouth, Mass.

[73] Assignee: Difco Laboratories, Ann Arbor, Mich.

[21] Appl. No.: 503,081

[22] Filed: Jul. 14, 1995

[51] Int. Cl.⁶ .................................................. C12M 1/36
[52] U.S. Cl. .......................... 435/286.4; 435/286.5; 435/288.2; 435/288.1; 435/297.5; 435/309.1; 422/100; 422/63; 141/31; 141/270
[58] Field of Search ................... 435/30, 286.1, 435/286.3, 286.4, 286.5, 286.7, 287.3, 288.1, 288.2, 288.5, 297.1, 297.5, 304.1, 304.2, 309.1; 422/58, 100, 99, 101, 102, 63; 141/35, 69, 192, 237, 270, 319, 31; 366/210, 211, 237, 239

[56] References Cited

U.S. PATENT DOCUMENTS

| | | | |
|---|---|---|---|
| 3,892,130 | 7/1975 | Winget et al. | 73/425.4 |
| 3,895,661 | 7/1975 | Praglin et al. | 435/288.5 |
| 4,073,693 | 2/1978 | Janin | 435/288.2 |
| 4,076,592 | 2/1978 | Bradley | 195/103.5 |
| 4,239,853 | 12/1980 | Bradley | 435/33 |
| 4,298,035 | 11/1981 | Hossom | 141/1 |
| 4,554,839 | 11/1985 | Hewett et al. | 73/864.16 |
| 4,623,008 | 11/1986 | Shibata et al. | 141/89 |
| 4,708,850 | 11/1987 | Husain | 435/288.5 |
| 4,738,773 | 4/1988 | Muller-Ruchholtz et al. | 209/214 |
| 4,754,786 | 7/1988 | Roberts | 141/1 |
| 4,770,853 | 9/1988 | Bernstein | 422/58 |
| 4,806,316 | 2/1989 | Johnson et al. | 422/100 |
| 5,089,233 | 2/1992 | DeVaney, Jr. et al. | 422/99 |
| 5,186,339 | 2/1993 | Heissler | 211/74 |
| 5,195,825 | 3/1993 | Ringrose | 366/213 |
| 5,241,992 | 9/1993 | Oehlbeck et al. | 137/897 |
| 5,272,926 | 12/1993 | Wilkins | 73/864.13 |
| 5,330,072 | 7/1994 | Ferri, Jr. et al. | 221/1 |
| 5,341,189 | 8/1994 | Helfer et al. | 354/324 |
| 5,360,721 | 11/1994 | Wilkins | 435/30 |
| 5,366,873 | 11/1994 | Eden et al. | 435/34 |
| 5,370,269 | 12/1994 | Bernosky et al. | 221/61 |

FOREIGN PATENT DOCUMENTS

| | | | |
|---|---|---|---|
| 320752 | 6/1989 | European Pat. Off. | 435/288.2 |
| 0345230B | 9/1994 | European Pat. Off. | A61J 1/00 |
| 2196117 | 4/1988 | United Kingdom | 435/34 |
| WO9107503 | 3/1991 | WIPO | C12Q 1/00 |
| WO9426414 | 11/1994 | WIPO | B01L 3/00 |

OTHER PUBLICATIONS

Dever et al., "Methods For The Detection of Foodborne *Listeria Monocytogenes* in the U.S." *Journal of Food Safety*, 13:263–292 (1993).

*Primary Examiner*—William H. Beisner
*Attorney, Agent, or Firm*—Kohn & Associates

[57] ABSTRACT

A system (100), methods and apparatuses for transferring a primary medium (7) after incubating of the medium (7) are described. The system (100) includes a container (1) for containing a growth medium (7) and a sample (8) to be tested for the presence of target microorganisms. A system (100) for transferring a primary medium (7) after incubating of the medium (7) is also described. The system (100) includes an automated pouring mechanism for automatically pouring the primary medium (7) into a plurality of media receiving vessels (11) and a metering mechanism for metering the amount of medium (7) poured into each media receiving vessel (11). An automated tilting apparatus (20) tilts the container (1) to actuate pouring of a predetermined amount of the medium (7) from the container (1) into the media receiver (11). An apparatus (20) for automatically transferring medium (7) for collection and testing of microorganisms is also described. It includes an automated tilting apparatus (20) for automatically tilting the container (1) to actuate pouring of a predetermined amount of medium (7) from the container (1) into a media receiver (11). A container (1) for transferring medium (7) for collection and testing of microorganisms is also described. A manifold (12) for controlling the flow of a primary medium (7) transferred from a from a container (1) to a receptacle vessel (11) is also described.

12 Claims, 4 Drawing Sheets

SYSTEM AND APPARATUS FOR AUTOMATICALLY TRANSFERRING MEDIA

BACKGROUND OF THE INVENTION

1. Technical Field

The present invention relates to an integrated system, and an apparatuses for detecting microbial growth from a sample substance and, more particularly, relates to a mechanism for automatically transferring of primary medium after a predetermined growth to multiple receptacles containing secondary media for testing of growth of target microorganisms in a sample.

2. Background Art

It is necessary to test various substances, such as food, pharmaceuticals, cosmetics, and water for microbial contamination with pathogenic organisms that might cause disease. A prime technique for screening for the presence of pathogens involves a series of media (nutrient fluid) transfers starting from non-selective, primary enrichment medium to selective media. This process allows for the initiation of growth of a potentially injured microorganism in the non-selective, primary enrichment media and, once the microorganism(s) has been revived a small quantity of the primary enrichment medium is transferred into several secondary (selective) media. This process, whose duration is often defined by human work patterns and growth patterns of the microorganisms, can take several days to complete when multiple transfers are required.

For example, culturing a food sample for the presence of Salmonella typically involves the addition of approximately twenty-five grams of sample, such as meat, into approximately 225 ml of primary enrichment broth. The primary enrichment medium is non-selective, such as Buffered Peptone Water (BPW) or Universal Preenrichment Broth (UPB), to allow for repair of injured organisms. The sample is thoroughly mixed with the primary enrichment broth and incubated for 22–28 hours at 35° C. Following this step, the sample is further enriched in a growth promoting medium containing inhibitors which would allow for the continued growth of a target organism, such as Salmonella, while simultaneously restricting the proliferation of most other bacteria. The most commonly used method for enrichment of the target organism requires transfer of approximately 1 ml of the primary enrichment broth into two tubes containing 10 ml of Selenite Cystine Broth and Tetrathionate Broth (AOAC), respectively, and incubating these tubes for 22–28 hours at 35° C. Other secondary enrichment media for Salmonella could include Rappaport-Vassiliadis (MSRV) Medium and Lauryl Tryptose Broth. Immunological methods could utilize M Broth as the secondary enrichment medium. This secondary enrichment step is followed by a detection step that could be accomplished by plating the secondary enrichment broth into 2–4 plated media or by utilizing other more rapid methods, such as immunological assays or DNA probes (all media available from Difco Laboratories, Detroit, Mich.).

Another prior art example includes the method for culturing Listeria. One major method is the U.S.D.A. method (Dever et al. 1993, J. Food Safety 13:263–292). This method includes primary enrichment in University of Vermont Media (UVM) or Listeria Enrichment Broth (LEB) for 20–24 hours at 30° C. The primary enrichment is followed by transfer of 0.1 ml into 10 ml of LEB with increased acriflavine and/or transfer of 0.1 ml into Fraser Medium or modified Fraser Broth (secondary enrichment) followed by incubation for 24–28 hours at 35° C. Positive cultures are then transferred to plated media. Other suitable non-selective media can include Buffered Peptone Water (BPW), Universal Preenrichment Broth (UPB) and Tryptic Soy Broth-Yeast Extract (TSB-YE) (all media available from Difco Laboratories, Detroit, Mich.).

Many attempts have been made to shorten the length of the primary enrichment step in order to reduce total assay time. Generally, it has been found that six (6) to twelve (12) hours of primary enrichment were required to obtain enough viable microorganisms for further testing. Additionally, since many laboratories are not staffed beyond eight (8) hours, a transfer from the primary medium to the second (selective) media which can occur in the middle of the night becomes impractical. The traditional method also requires multiple handling of the cultures which can increase the likelihood for contamination, subjects laboratory technicians to exposure to pathogens during transfer, makes it difficult to carry out simultaneous multi-culture transfers, and is higher in cost as it requires the culture transfer to be performed by human (non-automated) means.

The present invention provides a solution to the above-discussed problems by providing an automated system for transferring media for collection and testing of microorganisms.

A further advantage of multiple selective media is that they allow for preliminary determination of presence (or absence) of a target organism. Different inhibitory systems in conjunction with dyes and biochemical reactions (cleavage by enzymes, fermentation of sugars, degradation of amino and carboxyl groups, etc.) can be used to eliminate negative samples. Since approximately 99% of samples tested yield a negative result for the presence of target pathogens, the system of the present invention allows for immediate elimination of any further testing since a negative result in the secondary enrichment media is highly indicative of the absence of the target organism in the sample.

Many prior art references suggest a solution to the problem of transferring liquids from one vessel to several other. Most such systems are quite complex. A closed system, for example, shown in U.S. Pat. Nos. 4,076,592, issued Feb. 28, 1978, and 4,239,853, issued Dec. 16, 1980 both to Bradley, describes a method and apparatus for simultaneously introducing a sample from a reservoir into a plurality of substantially side-by-side test zones or chambers. A chemical substance is disposed in each test zone. The testing apparatus can then be manually rotated about an axis such that the liquid is conducted into each test chamber under the force of gravity. The purpose of the prior art devices is to transfer liquid from a main reservoir to a plurality of chambers. There is no incubation or growth step prior to transfer. As a result, they teach an entirely open system without regard to the issue of evaporation. Transfer of liquid vapors from one chamber can transfer contamination to another chamber. In other words, the prior art transfer systems are not closed systems. Also, in the prior art devices, most or all of the liquid is transferred from the main chamber to the test chambers. The prior art devices do not provide for the transfer of a small, predetermined amount of liquid from the large main chamber to the smaller test chambers. No prior art device allows for restricted or metered flow such that transfers of 0.1 ml to 0.5 ml from a 250 ml volume of primary medium can be made as opposed to transferring a total volume to the test chambers.

The present invention employs an automated approach to the transfer of a metered amount of enrichment medium containing microorganisms into receptacles containing selective growth media or reagents at a pre-determined period of time and solve the above-mentioned problems of the prior art devices, thereby, provides a substantial improvement over these known devices.

SUMMARY OF THE INVENTION AND ADVANTAGES

According to the present invention, there is provided a system (100), method, and apparatuses for transferring a primary medium (7) after incubating of the medium for testing of target microorganisms in a sample (8) substance. The system (100) includes a container (1) for holding a primary medium (7) and a sample (8) to be tested for the presence of target microorganisms, media receiving receptacles (11) operatively connected to the container (1) for receiving medium (7) poured therefrom. An automated tilting apparatus (20) supports the container (1) and allows for growth of microorganisms within the container (1) is also provided. The automated tilting apparatus (20) supports the container (1) for allowing growth of microorganisms within the container (1) for a pre-determined period of time and then tilts the container (1) to actuate pouring of a pre-determined amount of the primary media (7) from the container (1) into the media receiving receptacle (11).

The present invention further provides a system (100) for transferring a primary medium (7) after incubating the medium (7) which includes an automatic pouring mechanism for automatically pouring the primary medium (7) into a plurality of media receiving receptacles (11) and a metering mechanism for metering the amount of medium (7) poured into each media receiving receptacle (11).

The present invention further provides a method for transferring a primary medium (7) after incubating the medium (7) including the steps of automatically pouring the primary medium (7) into a plurality of media receiving vessels (11) while metering the amount of medium (7) poured into each media receiving vessel (11).

The present invention further provides a method for transferring medium (7) after incubation of the medium (7) which includes the steps of applying a sample (8) to be tested for the presence of microorganisms to a container (1) containing primary medium (7), incubating the sample (8) in the primary medium (7) for a pre-determined period of time, and automatically tilting the container (1) to pour a pre-determined amount of the primary medium (7) from the container (1) into at least one media receiving receptacle (11).

The present invention further includes a container (1) for transferring media (7) after incubation of the media (7) including a container (1) for containing a primary medium (7) and a sample (8) to be tested for the presence of target microorganisms, a media receiving receptacle (11) operatively connected to the container (1) for receiving media (7) poured therefrom, and at least one connector (15) operatively connecting the container (1) with a media receiving receptacle (11).

Also in accordance with the present invention, there is provided an apparatus (20) for automatically transferring a medium (7) after incubation. The apparatus (20) for supporting a container (1) containing primary medium (7) for allowing growth of target microorganisms in the container (1) for a pre-determined period of time and then automatically tilting the container (1) to actuate pouring of a pre-determined amount of primary medium (7) from the container (1) into a media receiving receptacle (11).

Also in accordance with the present invention, there is provided a manifold (12) for controlling the flow of a primary medium (7) transferred from a container (1) into at least one media receiving vessel (11). The manifold (12) includes at least one inlet (13) connected to a primary media containing container (1) for receiving the medium (7) from the container (1) and at least one outlet (14) for distributing the primary medium (7) connected to at least one media receiving vessel (11). The manifold also includes a metering mechanism for controlling the amount of flow from the container (1) to each media receiving vessel (11).

BRIEF DESCRIPTION OF THE DRAWINGS

Other advantages of the present invention will be readily appreciated as the same becomes better understood by reference to the following detailed description when considered in conjunction with the accompanying drawings wherein like references numbers having a prime symbol refer to like parts which are different embodiments of similar parts and wherein.

DETAILED DESCRIPTION OF THE PREFERRED EMBODIMENT

Figure 1:
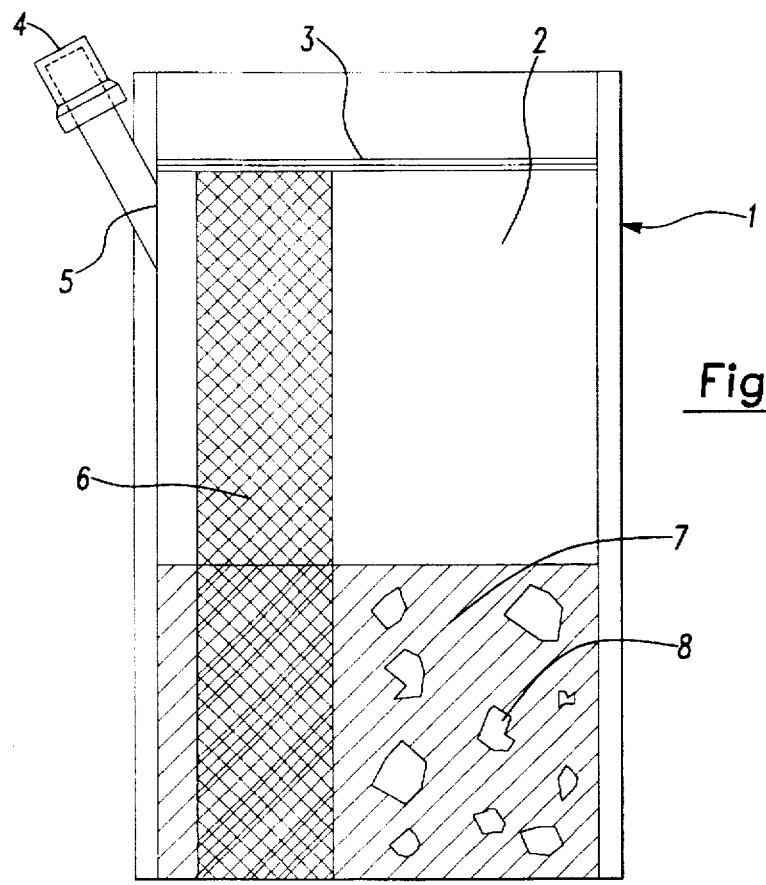
FIG. 1 is a side view illustrating the container of the present invention.

Generally, the present invention provides a system 100 for transferring growing organisms in primary enrichment medium 7 to one or more secondary enrichment media 17, the system 100 includes a container 1 for containing a growth medium 7 and a sample to be tested for the presence of target microorganisms. A receptacle 11 containing one or more secondary media 17 is operatively connected to the container 1 for receiving media 7 poured therefrom. An automated tilting apparatus 20 including a rack 22 is utilized for supporting the container 1 which includes the media 7 allowing growth of microorganisms within the container 1 for a predetermined period of time and then automatically tilting the container 1 to actuate pouring of a predetermined amount of the growth media 7 containing the target organism from the container 1 into the receptacle vial or vessel 11 containing secondary media 17. The amount poured into the vial(s) 11 is quite small compared to the amount of media contained in the container 1.

Target organisms are those organisms which are being specifically tested for and/or selected for using the system 100 of the present invention. For example, in testing a food sample, the target organisms which could be tested for could include, but are not limited to Salmonella and/or Listeria. Since these are particular pathogens which can be found in foods, they are "targeted" for testing in order to determine if they are present in a food sample.

Referring to FIG. 1, the primary enrichment container 1 is shown containing the primary growth media 7 and a sample 8. Container 1 is any container having a closed chamber 2 suitable for containing liquid microbiological growth media 7. The primary medium 7 can be provided in the chamber 2 in a pre-sterilized form, thereby eliminating the need for media preparation. Another option is to provide the growth medium 7 as a dried, low bioburden media (i.e., media not containing the target organism and which has a low total count) and add sterile water prior to the assay. In a preferred embodiment of the present invention, the container 1 is constructed in the form of a bag. The bag can be constructed of any suitable material such as polyester/polyethylene laminate and defines the chamber 2 therein. Because of the nature of the samples which may be tested, such as a food sample, the container 1 should be constructed of a resilient material so that it can withstand homogenizing or "stomaching" of the sample 8 disposed within the bag in order to expose microorganisms located within the sample 8. Container 1 can also be a bottle made out of glass or plastic. The primary medium 7 and the sample 8 are mixed prior to their addition to the container 1.

The container 1 can also include a closure 3 such as a "zip-lock" type closure to prevent spillage of the contents of the container 1 and, further, to prevent contamination of the contents of the container 1. In the case where a bottle is being used, the bottle requires a cap. Container 1 also includes a filter 6 sealed to the container 1. The filter 6 allows fluid to pass therethrough preventing the sample 8 particles from passing. The container 1 also includes a spout 5 and cap 4.

Figure 5:
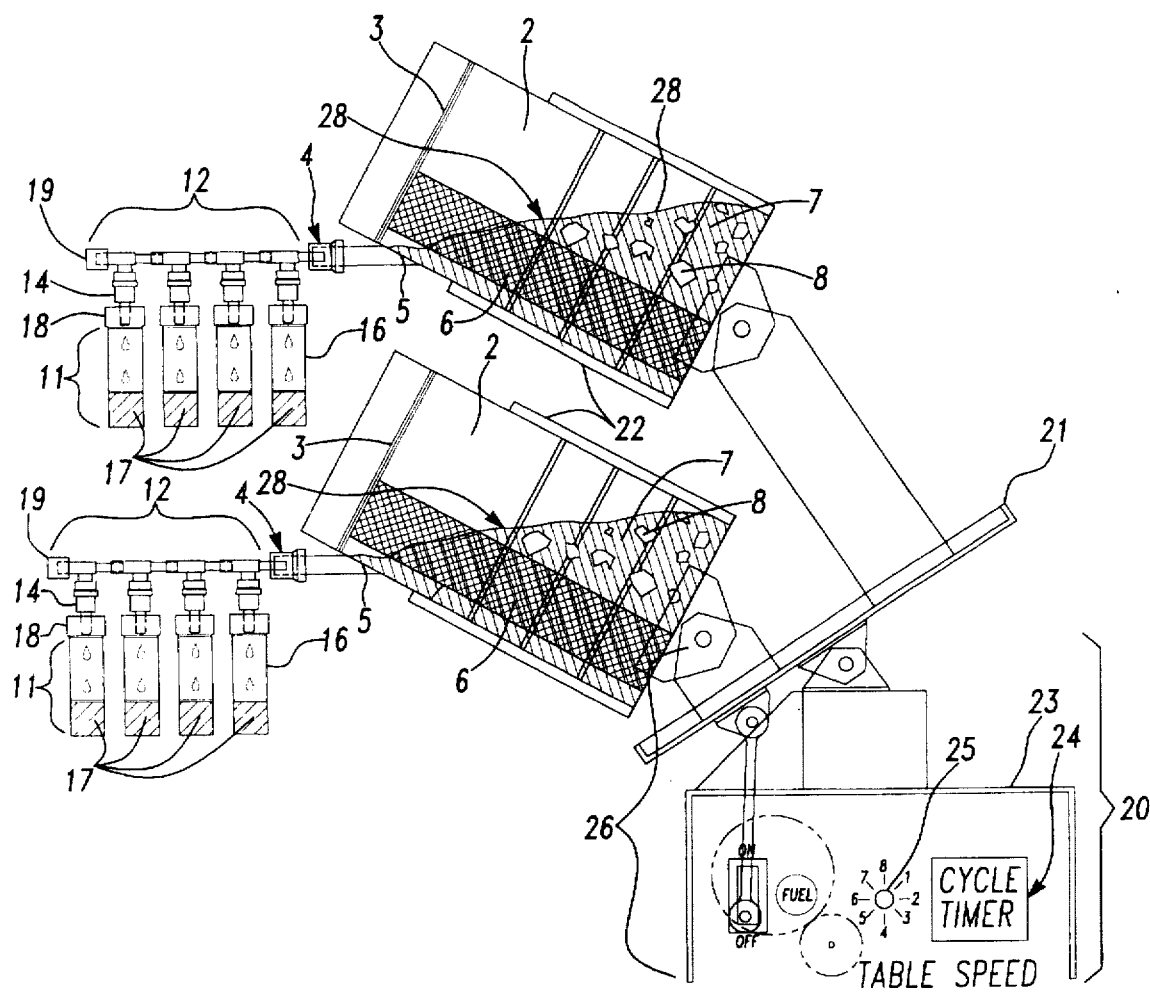
FIG. 5 illustrates the system of the present invention in a tilted orientation.

The receptacle vial 11 is constructed so as to be in fluid communication with the container 1. The receptacle 11 can be a separate compartment as shown in FIG. 2 formed within the container 1 adjacent to the chamber 2 or it can be externally located as shown in FIGS. 4 and 5.

In a second preferred embodiment of the present invention, the receptacle vial(s) 11 is externally located in fluid communication with the container 1. Referring to FIG. 3, the receptacle vial 11 can be connected to the container 1 via a manifold 12 which is either affixed or integrally formed with the container 1 and constructed of any suitable material, such as polypropylene. In this embodiment, the receptacle vial 11 is operatively connected to an opening 5 in the container 1 to which the opening 13 of the manifold 12 is attached.

Figure 2:
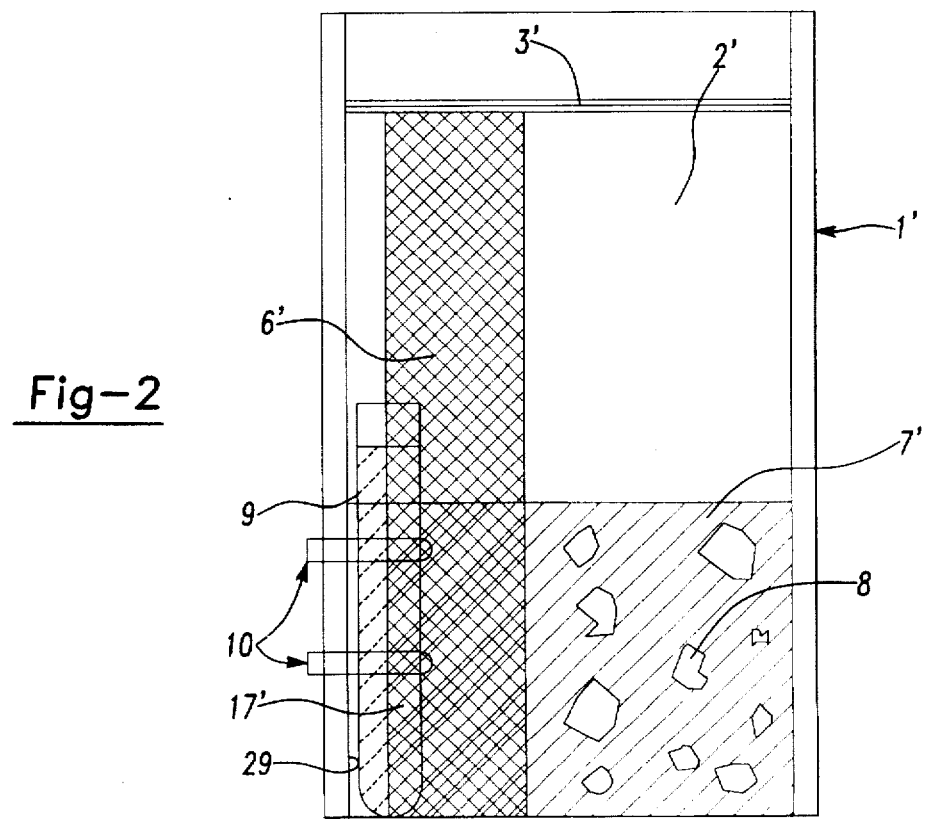
FIG. 2 is a side view illustrating an alternative embodiment of the container of the present invention.

Referring to FIG. 2, in the embodiment wherein the receptacle 9 and the sample 8' is located within the container 1' and includes a filter 6' and a closure 3'. The receptacle 9 can be formed by placing a barrier, such as a seam, or an outside vial can be clamped with clamps 10 to attach the vial 9 to the container 1'. The larger compartment of the two compartments defines the chamber 2' and would contain a primary enrichment medium 7'. The smaller compartment 29 defines the receptacle vial 9 and would contain a secondary or selective media 17'. The secondary media 17' can be pre-sterilized prior to its introduction into the container 1'. In this embodiment of the present invention, a sterile tube 9 could be inserted or attached into the smaller compartment 29 and the tube would contain the secondary media 17'.

Figures 3, 4:
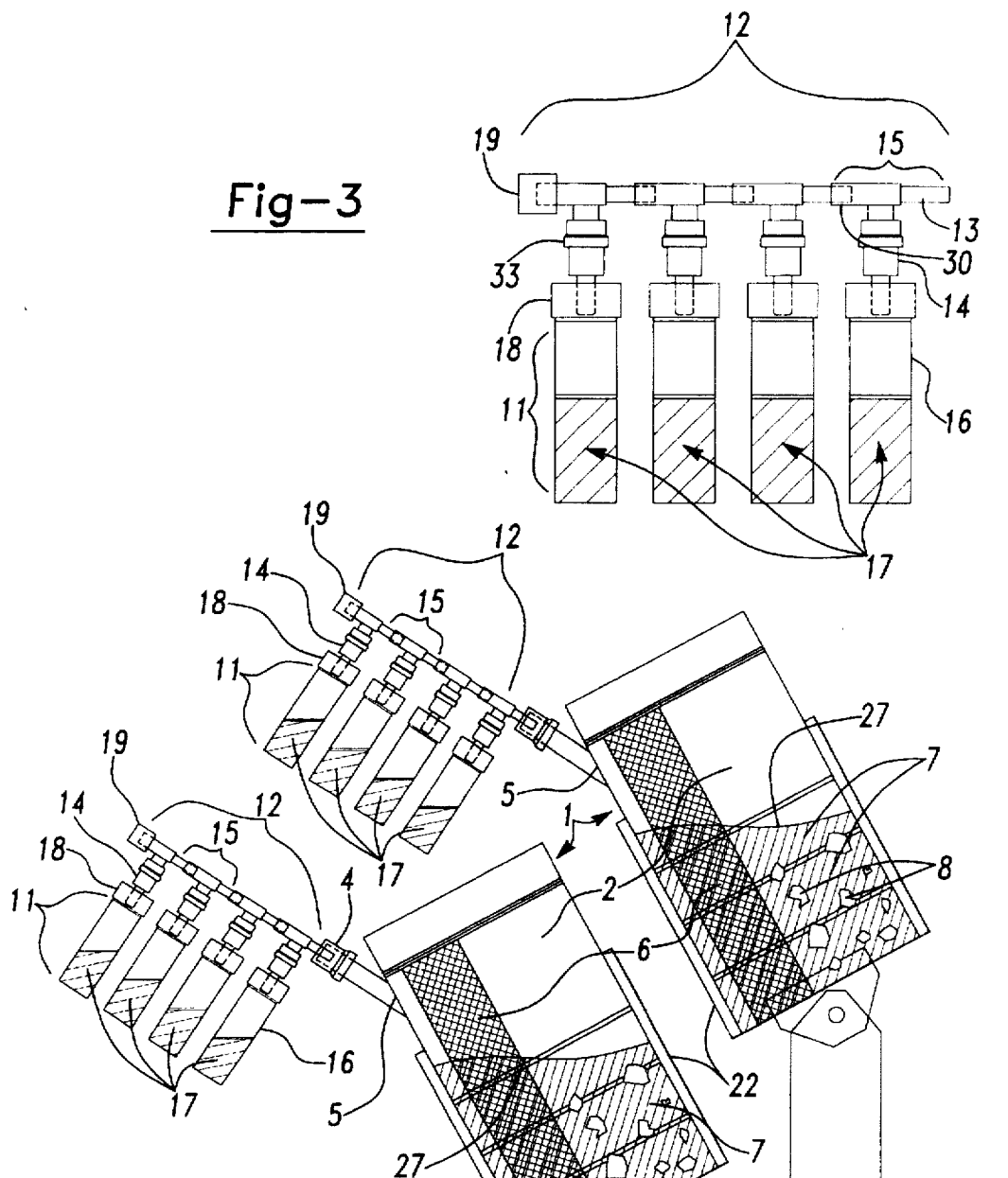
FIG. 3 is side view of connectors and media receivers of the present invention.
FIG. 4 illustrates the system of the present invention in a non-tilted orientation.

Referring to FIG. 3, the manifold 12 has an opening 13 and one or more three way connector units 15 and a closure 19. The three way connector 15 is connected to vial fitting 14 which connects the receptacle vial 11. The receptacle vial 11 has a vented cap 18, a glass or plastic tube 16, and contains a secondary enrichment media 17. The secondary media 17 can be pre-sterilized prior to introduction into the receptacle vial 11 or sterilized in the receptacle vial 11. The manifold 12 allows for the connection of at least one receptacle vial 11 to the container 1 in series or in parallel.

The manifold 12 can be extended to accommodate more than one receptacle vial 11 by utilizing three-way removable Luer-type connectors 15 in a male/female manner to extend the length of the manifold 12 as shown in FIG. 3. In this embodiment, a second outlet end 30 of the connector 15 is matingly engaged with another connector 15, thereby extending the length of the manifold 12.

The manifold 12 is used to meter or measure the amount or flow of medium 7 that is transferred into each receptacle vial 11. The bore size of the manifold 12 and opening size in the connectors 14 regulate the amount of medium 7 that is transferred by both gravity and by restricting the flow of medium 7 as a function of the surface tension of the medium 7. That is, the bore size and the opening size of the elements which make up the manifold 12 together with amount and/or duration of tilt, are designed to restrict the flow of medium 7 to such an extent that only a relatively small amount of media is allowed to enter into the receptacle vials 11. The metering or distribution function provided by the manifold 12 allows for only a small, well controlled transfer of the medium 7. Since only a very small amount of the primarily enriched medium 7 is need for further testing in the secondary media 17 in comparison to the large volume of medium 7 in the container 1, the manifold allows for precise transfer of these small amounts (approx. 0.1 ml to 0.5 ml).

The manifold 12 controls the amount of primary medium 7 transferred from the container 1 into each of the receptacle vials 11. The amount of medium 7 transferred into each receptacle 11 can be the same or different. That is, when more than one receptacle 11 is attached to the manifold 12, the manifold provides a mechanism by which, if desired, a different metered amount of medium 7 can be dispensed into each individual receptacle 11. Therefore, if several receptacles 11 are attached to the manifold 12 and each receptacle requires a different amount of medium 7 in order to perform a designated assay, the manifold 12 can be configured to allow the precise amount of medium 7 to be transferred into the receptacle 11 to perform that desired assay. In other words, by adjusting the flow rate through the manifold 12 to each individual receptacle 11, or by varying the duration of transfer of medium 7 to each individual receptacle 11, different metered amounts of medium 7 can be transferred to multiple receptacles 11 during a given transfer event. A transfer event being defined as pouring or transferring medium 7 from the container 1 to the receptacles 11. In other words, the transfer event could be accomplished by tilting the tilting apparatus 20 as described in greater detail below.

In this preferred embodiment, the receptacle vial 11 includes at least one tube 16 for containing a secondary or selective media 17 and for receiving growth medium 7 poured from the container 1. The receptacle vial 11 further includes a cover 18 which allows for attachment of the receptacle 11 to the connector 14 to place the receptacle 11 in fluid communication with the container 1. The receptacles 11 can be vials or test tubes having covers 18 which allow the vials or tubes to be connected and/or disconnected from the manifold 12 without breaching the sterility of the receptacle 11. The placement of the receptacles 11 containing the secondary media 17 outside the container 1 prevents contamination of the receptacles 11 and eliminates human contact with pathogens potentially present in the samples being tested.

The primary enrichment medium 7 can be any non-selective liquid growth medium which will allow for the recovery and growth of a potentially injured target organism and which will allow sufficient bacterial growth to allow for sufficient growth of the target organisms in such a way that the transferred volume will contain at least one viable target organism is such organism existed in the original sample 8. Examples of suitable non-selective growth media 7 (which are available from Difco Laboratories, Detroit, Mich.) include Tryptic Soy Broth (TSB), Buffered Peptone Water (BPW), Universal Preenrichment Broth (UPB), Lysteria Enrichment Broth (LEB), and other non-selective or mildly selective media known to those skilled in the art.

As stated above, the receptacle vial 11 can contain at least one reagent or secondary media 17, such as a selective media which aids in the detection or identification of particular microorganisms present in the sample 8 being tested. More specific examples of the secondary media 17 can include for Salmonella selection: Selenite Cystine, Tetrathoionate Broth, and Rapport-Vassiliades Broth. The secondary media 17 can further include media which allows for use of immunoassay or DNA probes such as M Broth. The secondary media 17 can also include antibiotics, dyes, and other biochemical indicators of particular microorganisms such as targeting sugar fermentation, decarboxylation, cleavage by unique enzymes, in combination with a unique combination of dyes (including fluorescent dyes). Other reagents or selective media 46 used in the detection and identification of microorganisms known to those skilled in the art may be practiced with the present invention.

The container 1 can further include a filter 6 for filtering particulate matter, such as food particles, from the growth medium 7 being transferred to the receptacle vial 11, thereby preventing potential clogging of the manifold 12 or receptacle vials 9 or 11. In preventing the transfer of particulate matter, the potential for particulate interference with any secondary media 17 is reduced or eliminated.

The filter 6 can be constructed of any suitable filter material such as hydrophobic 10 to 100 micron filter material. Pore or mesh size of the filter material can be selected to achieve exclusion of particulates greater in size than the maximum pore or mesh size. The filter material should be selected so that it is non-toxic to microorganisms and does not clog as a result of the presence of the sample 8.

Referring to FIGS. 4 and 5, the system 100 of the present invention further includes a tilting apparatus 20 which includes at least one platform 21 for supporting and retaining the container 1 or several such containers. The platform 21 further includes one or more racks 22 for supporting more than one container 1 at a time. The platform 21 is operatively connected to a base unit 23 which houses an electric motor timing device 24, table tilt mechanism 26, and a table speed controller 25. The platform 21 can move in order to agitate the samples 8 being tested. The platform 21 is tilted at least once per testing cycle to a first dispensing position and then is returned to its initial starting point or non-tilted configuration.

Additionally, the system 100 can be tilted in a second different or opposite direction ("reverse tilt") from the direction utilized for pouring or dispensing the primary medium 7 from the container 1 into at least one of the media receiving vessels 11. That is, the platform 21 can be tilted in a direction opposite the direction which causes transfer of the primary medium 7 from the container 1 into at least one of the media receiving vessels 11. The ability to tilt in the direction opposite of the direction of media transfer, can allow for the automated introduction of a substance, such as an inhibitor, into the primary enrichment media 7 after the target organisms have recovered from injury. The addition of a substance, such as antibiotics, bile salts such as sodium desoxycholate, and other substances to inhibit interfering flora following growth of viable target organisms can be used to make the primary enrichment medium 7 more selective. Following this "reverse tilt," at a desired time, the container 1 can be tilted to allow the transfer of the primary enrichment medium 7 into at least one media receiving vessel 11.

Figure 6:
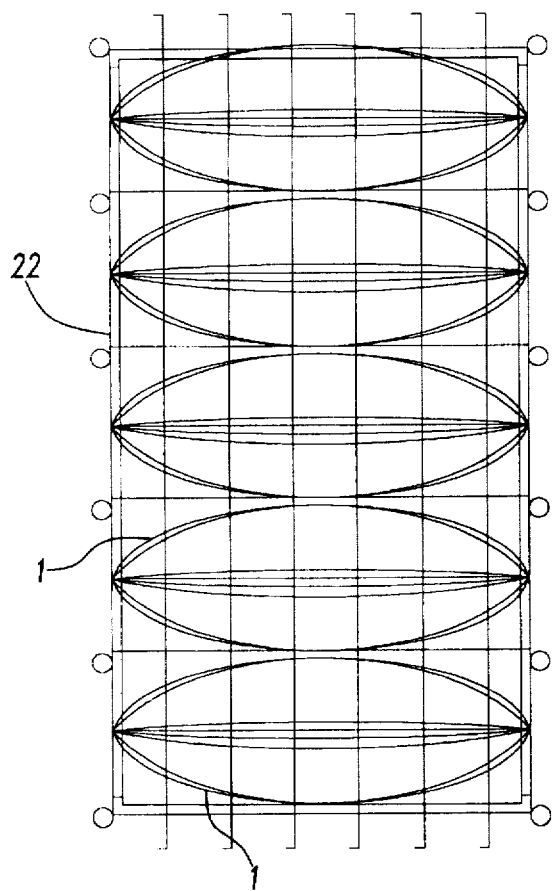
FIG. 6 is a top view of the present invention illustrating the rack containing a plurality of containers.
Figure 7:
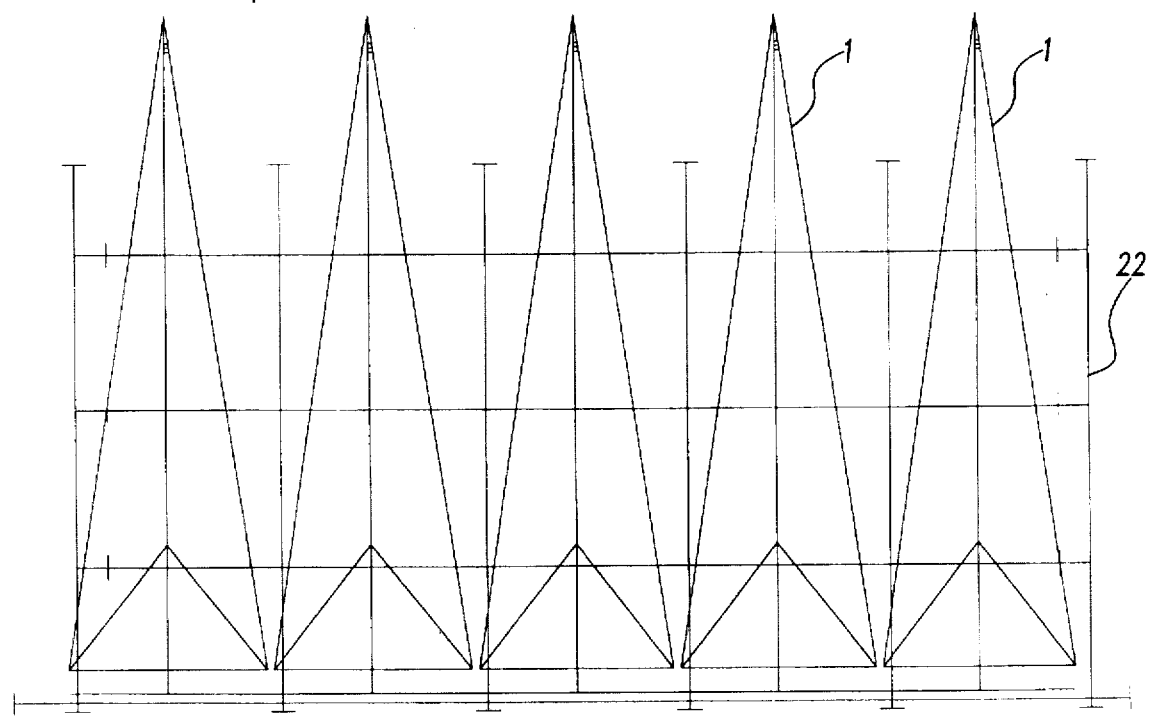
FIG. 7 is a side view illustrating the rack and containers of the present invention.

A platform 21 can be constructed to include multiple racks 22 as shown in FIGS. 6 and 7 so as to function in accordance with the present invention. Referring to FIGS. 6 and 7, a wire rack 22 contains multiple containers 1.

In operation, as shown in FIG. 4, the system 100 is shown in a non-pouring, neutral, or non-tilted position wherein the primary enrichment medium 7 resides entirely within a first compartment 2 of the container 1 and the level 27 of the primary enrichment medium 7 remains below the opening 5 in the manifold 12 to prevent transfer of any medium 7 to the receptacle vial 9 or 11. In this position, the platform 21 is horizontal or parallel with respect to base unit 23. In the preferred embodiment, the rack 21 holds the primary container 1 in a pre-tilted angle so as to require minimal tilting for liquid transfer At a predetermined time or at several, predetermined times, the timing device 24 causes the tilt mechanism 26 to move in a downward direction thereby automatically tilting the platform 21 in a downward direction to the tilted-position shown in FIG. 5.

In the tilted-position or dispensing position as shown in FIG. 5, the platform 21 is rotated with respect to the base unit 23. In the tilted-position or pouring position, the platform 21 and the base unit 23 are in an angled orientation with respect to each other. In the tilted-position, the container 1 is tilted into such an orientation so as to cause level 28 of the primary enrichment medium 7 to enter the opening in the spout 5 of the manifold 12. The tilting of the container 1 by the tilting apparatus 20, actuates the pouring of a predetermined amount of the primary enrichment medium 7 from the container 1 into the receptacle vials 11. The medium 7 flows under the force of gravity from the container 1 through the manifold 12 and is deposited into the receptacle vials 11 containing secondary media or reagents 17. Once the metered or predetermined amount of medium 7 has been poured from the container 1 into the receptacle vials 11, the platform can then be tilted back to a non-pouring position to stop the transfer of medium 7. This cycle can be carried out any number of times to fill only a desired number of receptacles 11 at any given time. Through the use of valve mechanisms (not shown), the transfer of medium 7 into a given receptacle 11 or group of receptacles 11 can be controlled to take place at a precisely determined time. That is, by controlling the transfer of medium 7 into the receptacles, by way of valves for example, the system 100 can be utilized to automatically perform tests which may have longer or shorter testing durations. By having the ability to automatically perform multiple transfers (i.e., multiple tilting or pouring operations) of the medium 7 into separate testing receptacles 11 over a long period of time, the system 100 allows for many more automated tests and operations to be performed in a given time interval. Multiple transfers of medium 7 allow for the transfer or the dispensing of small volumes of medium 7 into the secondary media 17 and, therefore, the timing of the transfer becomes less critical since the target organisms will have longer periods of time to grow in the medium 7 before they are transferred. Dispensing small amounts of medium 7 over time ensures that a sufficient amount of organisms will be transferred to the secondary media 17 to allow for identification of target organisms.

The terms "automated transfer" and "automatic tilting" are used herein to mean that the transfer of the primary enrichment medium 7 from the container 1 to the receptacle vials 11, at a predetermined time, is initiated by a self-operating mechanism which does not require any human intervention to effectuate the transfer. That is, the transfer of medium 7 is only caused by the tilting of the container 1 and not by any human manipulation. Furthermore, the mechanism described above for the automated transfer of medium 7, once set in motion, will, cause the transfer of medium 7 from the container 1 to the receptacle vials 11 without any outside intervention.

The present invention further includes a method for transferring primary enrichment medium 7 presumably containing microorganisms to a secondary media or reagent which includes the steps of applying a sample 8 to be tested for the presence of target microorganisms to the container 1 containing suitable primary enrichment medium 7. The sample 8 may be processed prior to or following its application to the container 1 containing the primary enrichment medium 7. The processing can include homogenizing or breaking up the sample 8 to expose more surface area of the sample 8 where microorganisms may be present. The sample 8 can also be processed within the container 1 by homogenizing or "stomaching" the samples 8 directly in the container 1 by placing the container 1 in a machine (not shown) which provides reciprocating paddles which apply a controlled pressure to the sample 8 to blend or homogenize the sample 8 into a suspension (Tekmar, available from Thomas Scientific, Swedesboro, N.J.).

The container 1 containing the sample 8 and the primary enrichment medium 7 is then placed into the rack 21 which is connected to the tilting apparatus 20. The tilting apparatus 20 is disposed in its neutral or horizontal position which prevents the transfer of primary enrichment medium 7 from the container 1 to the receptacle vials 11.

The container 1 containing the sample 8 disposed in the primary enrichment medium 7 is then incubated for a predetermined period of time and at a preselected temperature in order to facilitate growth of target microorganisms present in the sample 8. During the incubation step, the container 1 may or may not be agitated or rocked in order to aerate the medium 7.

At a predetermined time, for example, six to ten hours from application of the sample 8 to the container 1, the timing device 24 triggers the tilt mechanism 26 causing the platform 21 to rotate into the tilted-position where the platform 21 is now angled with respect to the base unit 20. In this orientation, a predetermined amount of the medium 7 from the container 1 can flow from the container into the manifold 12 where it is distributed into the receptacle vials 11 containing secondary media 17.

The method can further include at least one additional step of rotating or tilting the platform 21 in a direction opposite the dispensing direction in order to allow for the addition of other substances, such as inhibitors, to be dispensed into the medium 7 to make the primary enrichment medium 7 more selective or inhibitory to growth of non-target organisms present in the sample 8.

As stated above, the method can include multiple transferring or dispensing steps which allow for at least one transfer of primary enrichment medium 7 to be dispensed into the receptacle vials 11.

The receptacle vials 11 containing the secondary media 17 can then be further incubated in order to detect or identify target microorganisms present in the sample 8. The detection step may be carried out either visually, such as a subjective determination of turbidity, a color change, or by utilizing any immunodiagnostics, nucleic acid detection or any mechanical means of the detection known in the art such as spectrophotometric analysis of the media in the receptacle vials 11.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

REFERENCES CITED

Dever et al., J. Food Safety 13:263-292 (1993).

What is claimed is:

1. A system (100) for transferring a primary medium (7) after incubating the medium, said system (100) comprising:

container means (1) for containing a primary medium (7) and a sample (8) to be tested for the presence of target microorganisms;

media receiving means (11) operatively connected to said container means (1) for receiving medium (7) poured therefrom; and automated tilting means (20) supporting said container means (1) for allowing growth of microorganisms within said container means (1) for a predetermined period of time and then tilting said container means (1) to actuate pouring of a predetermined amount of said medium (7) from said container (1) into said media receiving means (11) and then returning said container means (1) to a non-pouring position, wherein said tilting means (20) further includes actuating means (26) for actuating dispensing of a predetermined amount of said medium (7) from said container means (1) into said media receiving means (11) and timing means (24) operatively connected to said actuating means (26) for actuating pouring of a predetermined amount of said medium (7) from said container means (1) into said media receiving means (11) at a predetermined time, said predetermined amount of said medium being less than the total amount of medium contained within said container means.

2. A system (100) as set forth in claim 1, wherein said tilting means (20) further includes at least one rack (22) for supporting and retaining said container means (1).

3. A system (100) as set forth in claim 1, wherein said tilting means (20) tilts said container means (1) in a second direction different than the first mentioned direction to actuate dispensing of a predetermined amount of a substance into said container (1) and then returning said container means (1) to a non-pouring position.

4. A system (100) as set forth in claim 3, wherein the second direction is opposite the first mentioned direction.

5. A system (100) as set forth in claim 3, wherein said substance is a selected from the group consisting essentially of growth inhibitors, selective media, dyes, antibiotics, and bile salts.

6. A system (100) as set forth in claim 1, wherein said media receiving means (11) includes at least one reagent (17) which will allow for detection or identification of microorganisms in the sample (8).

7. A system (100) as set forth in claim 1, wherein said container means (1) includes connection means (12) operatively connecting said container means (1) with said media receiving means (11).

8. A system (100) as set forth in claim 7, wherein said connection means (12) permits attachment of at least two media receiving means (11) to said connecting means (12).

9. A system (100) as set forth in claim 8, wherein said at least two media receiving means (110) are connected to said connecting means (12) in parallel.

10. A system (100) as set forth in claim 8, wherein said at least two media receiving means (11) are connected to said connecting means (12) in series.

11. A system (100) as set forth in claim 1, wherein said media receiving means (9) is located within said container means (1).

12. A system (100) as set forth in claim 1, wherein said container means (1) includes filter means (6) for filtering said growth medium (7) during transfer of said growth medium (7) from said container means (1) to said media receiving means (11).

* * * * *